(12) United States Patent
Saito

(10) Patent No.: US 7,851,755 B2
(45) Date of Patent: Dec. 14, 2010

(54) APPARATUS FOR DETECTING BACKSCATTERED ELECTRONS IN A BEAM APPARATUS

(75) Inventor: Manabu Saito, Tokyo (JP)

(73) Assignee: Jeol Ltd., Tokyo (JP)

( * ) Notice: Subject to any disclaimer, the term of this patent is extended or adjusted under 35 U.S.C. 154(b) by 230 days.

(21) Appl. No.: 11/961,263

(22) Filed: Dec. 20, 2007

(65) Prior Publication Data

US 2008/0149831 A1 Jun. 26, 2008

(30) Foreign Application Priority Data

Dec. 20, 2006 (JP) .............................. 2006-342618
Apr. 2, 2007 (JP) .............................. 2007-096405

(51) Int. Cl.
*H01J 37/26* (2006.01)
*G21K 5/04* (2006.01)
(52) U.S. Cl. ...................... 250/310; 250/306; 250/307; 250/396 R; 250/492.3
(58) Field of Classification Search ............. 250/396 R, 250/396 ML, 306, 307, 309, 310, 311, 397, 250/399, 492.1, 492.2, 492.21, 492.3, 491.1, 250/492.22; 430/296, 297, 298, 299
See application file for complete search history.

(56) References Cited

U.S. PATENT DOCUMENTS

| | | | | |
|---|---|---|---|---|
| 4,424,448 A | * | 1/1984 | Takigawa et al. ............. | 250/397 |
| 2003/0089859 A1 | * | 5/2003 | Adamec ............... | 250/396 ML |
| 2003/0155509 A1 | * | 8/2003 | Nakasuji et al. ............. | 250/310 |
| 2005/0104006 A1 | * | 5/2005 | Yoshida et al. ........... | 250/396 R |
| 2006/0145087 A1 | * | 7/2006 | Parker .................... | 250/396 R |
| 2006/0243908 A1 | * | 11/2006 | Shinada et al. ............... | 250/310 |
| 2007/0040118 A1 | * | 2/2007 | Cheng et al. ................ | 250/310 |
| 2007/0120071 A1 | * | 5/2007 | Steigerwald et al. ...... | 250/492.1 |
| 2008/0035853 A1 | * | 2/2008 | Doering et al. ........ | 250/396 ML |
| 2008/0121810 A1 | * | 5/2008 | Liu et al. .............. | 250/396 ML |
| 2008/0308729 A1 | * | 12/2008 | Kimba et al. ............... | 250/307 |

FOREIGN PATENT DOCUMENTS

| | | |
|---|---|---|
| JP | 09-219170 | 8/1997 |
| JP | 2000-030654 | 1/2000 |
| JP | 3136353 | 8/2000 |
| JP | 2000-299078 | 10/2000 |
| JP | 2004-221089 | 8/2004 |

\* cited by examiner

*Primary Examiner*—Jack I Berman
*Assistant Examiner*—Nicole Ippolito Rausch
(74) *Attorney, Agent, or Firm*—The Webb Law Firm

(57) ABSTRACT

A beam apparatus has a beam source producing a primary electron beam, an objective lens focusing the beam onto an observed sample, and at least one condenser lens mounted between the beam source and the objective lens. The condenser lens operates such that the beam forms one crossover point between the condenser lens and the objective lens. A first detector is mounted at the crossover point or at a position closer to the sample than the crossover point. A second detector is mounted at a position closer to the electron source than the crossover point.

9 Claims, 13 Drawing Sheets

APPARATUS FOR DETECTING BACKSCATTERED ELECTRONS IN A BEAM APPARATUS

BACKGROUND OF THE INVENTION

1. Field of the Invention

The present invention relates to a beam apparatus, such as a scanning electron microscope and, more particularly, to a beam apparatus capable of detecting backscattered electrons and secondary electrons separately.

2. Description of Related Art

FIG. 6 is a diagram showing an example of structure of the electron optical system of a beam apparatus, such as a scanning electron microscope. The scanning optics are omitted. The apparatus has an electron source 1 acting as a beam source. A primary electron beam 2 is emitted from the electron source 1. The beam 2 is accelerated to a desired accelerating voltage by acceleration electrodes (not shown). Then, the beam is shaped into a perfectly circular cross section by a beam-shaping aperture 7. Subsequently, the beam 2 is focused by an objective lens 4 and controlled such that the beam is brought to a focus at the surface of a sample 5 to be observed. Under this condition, the beam is scanned in two dimensions over the observed sample 5 using scanning deflectors (not shown). Produced signals, i.e., secondary electrons and backscattered electrons, are detected. A scanned image is created.

Normally, the beam-shaping aperture 7 has a function of limiting the beam current. It is possible to increase and reduce the beam current by varying the intensity of a lens (not shown) present between the aperture 7 and the electron source 1. If control is provided to increase or reduce the beam current in this way, the position of a virtual light source as viewed from the objective lens 4 varies. This makes it impossible to correctly control the angular aperture with the objective lens 4. The resolution of the scanned image depends on the diameter of the beam on the observed sample 5, but the beam diameter strongly depends on the angular aperture.

When the angular aperture has an optimum value, the smallest beam diameter is obtained, and the resolution of the scanned image is improved maximally. Accordingly, variation in the position of the virtual light source can be corrected using the condenser lens 3. As a result, the primary electron beam 2 can be brought to a focus on the observed sample 5 at the correct angular aperture.

The configuration and operation of a prior art charged-particle detector are illustrated in FIGS. 7 and 8. FIG. 7 is a diagram showing the prior art charged-particle detector and the orbit of secondary electrons. FIG. 8 is a diagram showing a prior art charged-particle detector and the orbit of backscattered electrons. In FIGS. 6, 7, and 8, identical components are indicated by identical reference numerals.

Secondary electrons 10 emitted from the observed sample 5 have various directions and various energies. The electrons travel while describing some trajectory depending on the field produced by the objective lens 4 and on the fields produced by peripheral structures. It is possible to make the secondary electrons 10 travel toward a charged-particle detector 8 within the lens by appropriately designing the objective lens 4 and peripheral structures.

In FIG. 7, the secondary electrons 10 are lower in energy than the primary electron beam 2 and, therefore, undergo a larger focusing action in the magnetic field set up by the objective lens 4. The beam 2 creates 0, 1, or more crossover points. If the orbit of the secondary electrons 10 at the location where the beam leaves the magnetic field is in a divergent direction, the beam arrives at the charged-particle detector 8, creating a scanned image signal. Usually, the position at which the secondary electron detection efficiency is optimized is determined by electron optics simulations or experiments, and the detector 8 is arranged.

In FIG. 8, backscattered electrons 9 have energies almost equal to the primary electron beam 2 and, therefore, do not undergo a large focusing action from the magnetic field produced by the objective lens 4. Accordingly, the backscattered electrons 9 arrive at the charged-particle detector 8 without creating any crossover. The detector 8 is provided with a hole 8a to permit passage of the primary electron beam 2. Where the diameter of the backscattered electrons 9 is larger than the diameter of the hole 8a, the backscattered electrons 9 are detected by the detector 8, resulting in a scanned image signal.

The angular aperture of the primary electron beam 2 is 5 to 10 mrad. It is considered that the backscattered electrons 9 have an angle of emergence that is several times larger than the angular aperture and, therefore, the scanned image signal contains a backscattered electron signal. Consequently, the output signal from the charged-particle detector 8 represents secondary electrons plus some of the backscattered electrons. The difference between secondary electrons and backscattered electrons is now described. Secondary electrons have lower energies and thus are adapted to capture an image of the surface of the observed sample. Backscattered electrons have higher energies and so penetrate into the observed sample to some extent. The backscattered electrons are adapted to grasp the composition of the sample.

A prior art apparatus of this kind has a light source-side detector and a sample-side detector on the optical axis. The detectors detect almost all secondary electrons emanating from the sample (see, for example, JP-A-2000-30654 (paragraphs 0021-0026, FIGS. 1 and 2)). Furthermore, an apparatus having first and second detectors for detecting secondary electrons or backscattered electrons produced based on the interaction between the primary electron beam and the sample is known (see, for example, JP-A-2004-221089 (paragraphs 0035-0037, FIG. 2)). In addition, an apparatus having a simple structure and capable of detecting secondary electrons and backscattered electrons from the sample separately is known (see, for example, JP-A-2000-299078 (paragraphs 0020-0033, FIGS. 1-5)). Further, an apparatus having first and second detectors and capable of detecting secondary electrons is known. The first detector detects secondary electrons emitted from the sample, while the second detector detects secondary electrons passed through a hole in the first detector. The secondary electrons are detected by combining the output signals from the two detectors (see, for example, Japanese Patent No. 3,136,353 (paragraphs 0024-0037, FIGS. 1 and 2) and JP-A-9-219170).

With the above-described prior art, it has been difficult to detect secondary electrons and backscattered electrons separately. More correctly speaking, it has been difficult to detect secondary electrons and backscattered electrons separately and simultaneously, for the following reason. The output signal from the charged-particle detector 8 is the sum of a signal indicating secondary signals and a signal indicating some of the backscattered electrons as described previously.

If it is not necessary to have simultaneity, only backscattered electrons can be detected, for example, by using a detector that is insensitive to secondary electrons (e.g., a semiconductor detector). That is, secondary electrons and backscattered electrons impinge on the semiconductor detector. Because the detector is insensitive to the secondary electrons, only the backscattered electrons can be detected as a consequence.

It is also customary to place a deflector at the position of a detector such that only secondary electrons having low energies are bent and arrive at the detector. If the deflector is operated, backscattered electrons cannot be bent because they have higher energies. Therefore, only secondary electrons can be bent and made to arrive at the detector. However, if simultaneity is obtained, the throughput will be improved easily.

The detector insensitive to secondary electrons has another disadvantage. This detector is insensitive to backscattered electrons in a case where the energies of the primary electron beam are low because, in this case, the energies of backscattered electrons are lower.

SUMMARY OF THE INVENTION

It is an object of the present invention to provide a beam apparatus which can detect backscattered electrons of low energies and which can detect backscattered electrons and secondary electrons separately and simultaneously.

Furthermore, in the prior art, the diameter of the hole 8a in the charged-particle detector 8 that forms a passage for the primary electron beam 2 is sometimes set greater than the diameter of the range of the orbit of backscattered electrons 9. In these cases, it has been difficult to detect backscattered electrons 9 emitted from the observed sample 5.

More specifically, the diameter of the hole 8a in the charged-particle detector 8 that forms a passage for the primary electron beam 2 is set to at least about 500 µm to 1 mm to avoid collision with the primary electron beam 2. In contrast, the diameter of the beam of the backscattered electrons 9 may be about hundreds of micrometers.

The diameter of the hole 7a in the beam-shaping aperture 7 disposed between the electron source 1 and the condenser lens 3 to permit passage of the primary electron beam 2 is about 30 µm. Therefore, if a signal produced based on the backscattered electrons arriving at the aperture 7 can be detected efficiently, it follows that the backscattered electrons can be detected efficiently.

The present invention has been made also in view of this point. It is another object of the present invention to provide a beam apparatus capable of detecting backscattered electrons efficiently and thus can obtain a sample image in which compositional information about the observed sample is sufficiently reflected.

A beam apparatus according to a first embodiment of the present invention has: a beam source for producing a primary beam; an objective lens for focusing the primary beam produced from the beam source onto a sample; and at least one condenser lens disposed between the beam source and the objective lens. The condenser lens operates such that the primary beam forms one crossover point between the condenser lens and the objective lens. A charged-particle detector is mounted at a position closer to the beam source than the crossover point. An aperture is disposed at the crossover point or at a position closer to the observed sample than the crossover point.

A beam apparatus according to a second embodiment of the present invention has: a beam source for producing a primary beam; an objective lens for focusing the primary beam produced from the beam source onto a sample; and at least one condenser lens disposed between the beam source and the objective lens. The condenser lens operates such that the primary beam forms one crossover point between the condenser lens and the objective lens. A first charged-particle detector is mounted at the crossover point or at a position closer to the sample than the crossover point. A second charged-particle detector is mounted at a position closer to the beam source than the crossover point.

A beam apparatus according to a third embodiment of the present invention has: a beam source for producing a primary beam; an objective lens for focusing the primary beam produced from the beam source onto a sample; and at least one condenser lens disposed between the beam source and the objective lens. The condenser lens operates such that the primary beam forms one crossover point between the condenser lens and the objective lens. A charged-particle detector is mounted at the crossover point or at a position closer to the sample than the crossover point.

A beam apparatus according to a fourth embodiment of the present invention has: a beam source for producing a primary beam; an objective lens for focusing the primary beam produced from the beam source onto a sample; and an aperture disposed between the beam source and the objective lens. The apparatus further includes a detector and a hollow electrode. Secondary particles produced secondarily from the sample in response to the beam irradiation arrive at the aperture. Particles produced from the aperture by an interaction between the secondary particles and the aperture are detected by the detector. The center axis of the hollow electrode is located on the optical axis of the primary beam emitted from the beam source. The electrode has an opening at its one side located opposite to the detector. The electric field produced by the electrode moves the particles emanating from the aperture toward the detector through the opening. Thus, the moved particles are detected by the detector.

According to the beam apparatus of the first embodiment, backscattered electrons pass through the aperture and can arrive at the charged-particle detector. Secondary electrons are blocked by the aperture. Accordingly, only the backscattered electrons can be separated out and detected. A backscattered electron image of low energies can be obtained, which has been impossible to achieve.

According to the beam apparatus of the second embodiment, backscattered electrons and secondary electrons can be detected separately and simultaneously.

According to the beam apparatus of the third embodiment, secondary electrons can be detected efficiently by the charged-particle detector.

In the beam apparatus of the first through third embodiments, a magnetic objective lens is used as the objective lens. A sharply focused electron beam can be made to hit the sample.

Furthermore, in the beam apparatus of the first through third embodiments, an image with reduced aberration can be obtained by using a cathode lens as the objective lens.

Moreover, in the beam apparatus of the first through third embodiments, an image with still reduced aberration can be obtained by using a combined magnetic objective lens-cathode lens as the objective lens.

In addition, in the beam apparatus of the first through third embodiments, an image with reduced aberration can be obtained by using a combined magnetic objective lens-decelerating electrostatic objective lens as the aforementioned objective lens.

Further, in the beam apparatus of the first through third embodiments, an image with reduced aberration can be obtained by using a combined magnetic objective lens-cathode lens as the objective lens.

Moreover, in the beam apparatus of the first through third embodiments, the primary electron beam can be shaped into a perfectly circular cross section by providing a beam-shaping aperture over the condenser lens. An accurate image can be obtained by limiting the beam current of the primary electron beam.

In the fourth embodiment, the detector for detecting particles produced from the aperture by an interaction between the secondary particles and the aperture after the secondary particles arrive at the aperture is provided, the secondary particles being produced secondarily from the sample in response to the irradiation by the primary beam. The hollow electrode whose center axis is located on the optical axis of the primary beam produced from the beam source is provided. The aperture in the electrode is formed at its one side located opposite to the detector. The particles from the aperture are moved toward the detector through the aperture by the action of the electric field produced by the electrode. The moved particles are detected by the detector.

The particles to be detected can be attracted toward the detector by the action of the electric field produced by the electrode. Therefore, a signal produced based on the secondary particles (particles to be detected) arriving at the aperture from the sample can be detected efficiently. As a result, the secondary particles can be detected efficiently.

Where the secondary particles are backscattered electrons, the signal produced based on the backscattered electrons can be detected efficiently. As a result, the backscattered electrons can be detected efficiently.

These and other objects and advantages of the present invention will become more apparent as the following description proceeds.

DETAILED DESCRIPTION OF THE INVENTION

The preferred embodiments of the present invention are hereinafter described in detail with reference to the drawings.

First Embodiment

Figure 1:
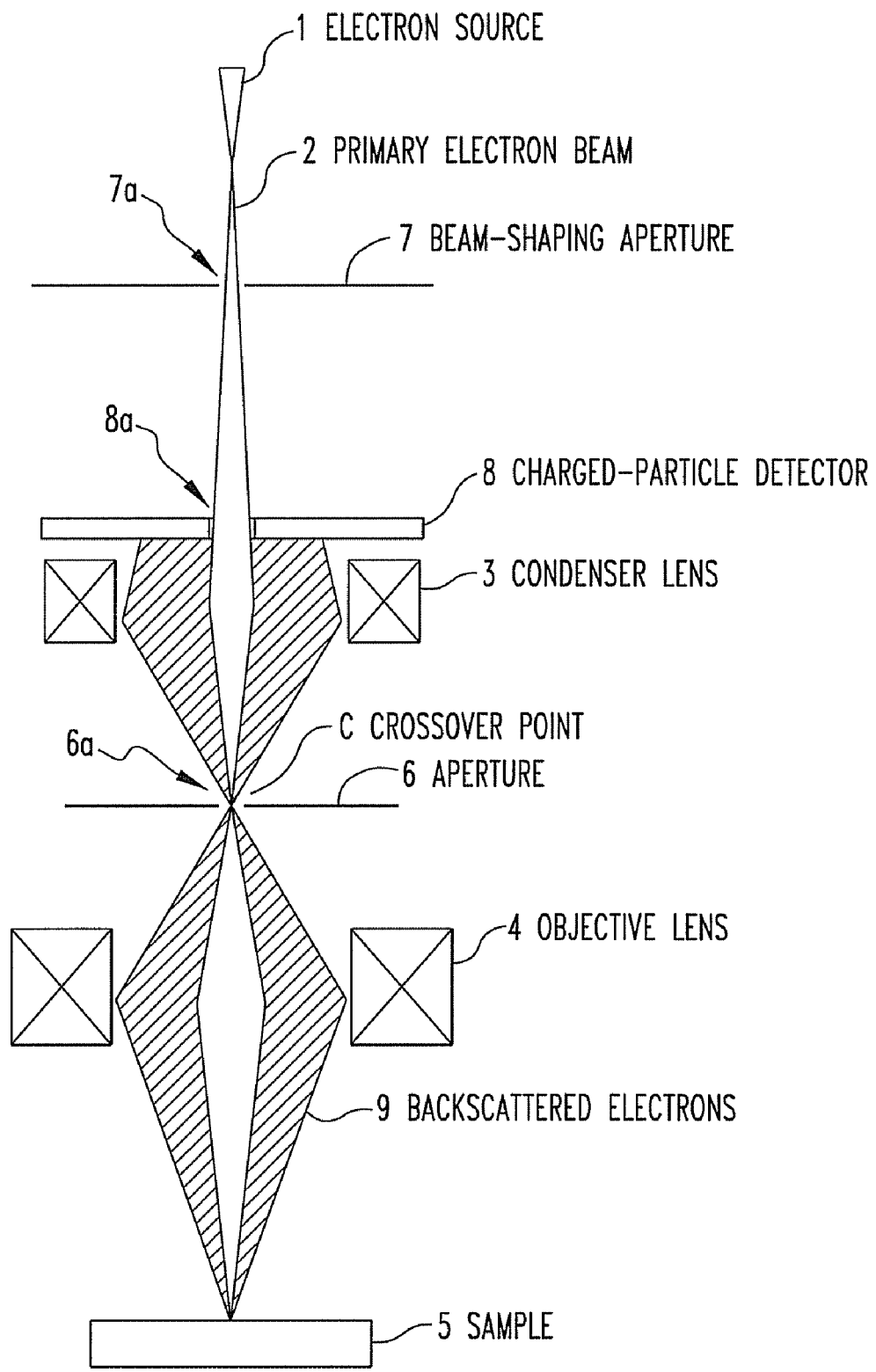
FIG. 1 is a diagram illustrating the orbit of backscattered electrons in a beam apparatus according to a first embodiment of the present invention.
Figure 2:
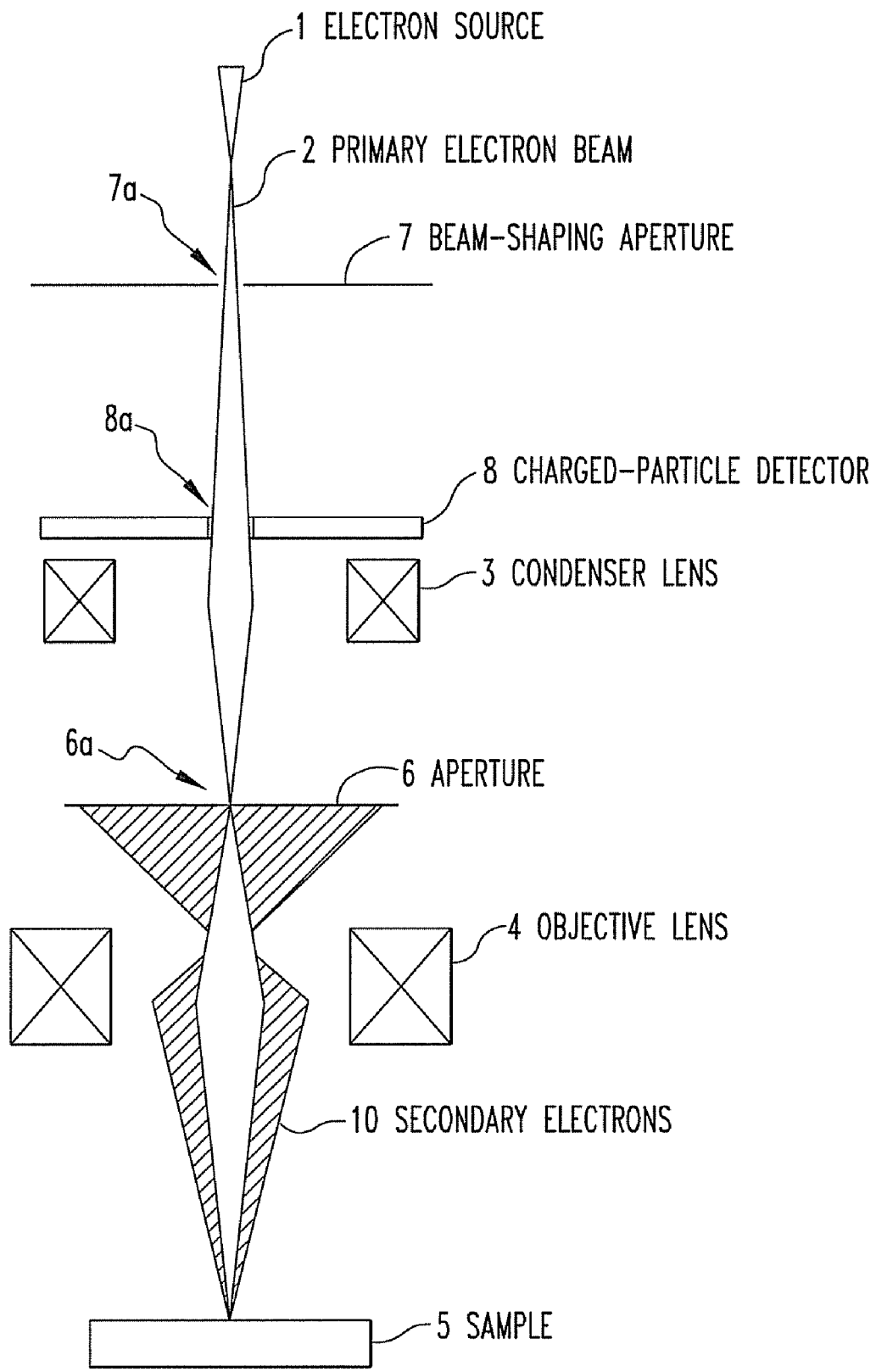
FIG. 2 is a diagram illustrating the orbit of secondary electrons in the beam apparatus according to the first embodiment of the present invention.

A first embodiment of the present invention is illustrated in FIGS. 1 and 2. FIG. 1 is a diagram showing the orbit of backscattered electrons in a beam apparatus according to the first embodiment of the present invention. FIG. 2 is a diagram showing the orbit of secondary electrons in a beam apparatus according to the first embodiment of the present invention. In FIGS. 1-2 and 6-8, identical components are indicated by identical reference numerals. The scanning optics are omitted. In FIG. 1, the apparatus has an electron source 1 acting as a beam source. A primary electron beam 2 is emitted from the electron source 1. The beam 2 is focused by an objective lens 4 onto a sample 5 to be observed. At least one condenser lens 3 is disposed between the electron source 1 and the objective lens 4. The beam 2 is shaped into a perfectly circular cross section by a beam-shaping aperture 7. The aperture 7 also acts to limit the beam current of the primary electron beam.

The condenser lens 3 operates such that the primary electron beam 2 forms one crossover point between the condenser lens 3 and the objective lens 4. A charged-particle detector 8 is mounted at a position closer to the electron source than the crossover point, and has a hole 8a. An aperture 6 is mounted at a position closer to the observed sample 5 than the crossover point, and has an opening whose diameter is larger than that of the primary electron beam. Backscattered electrons 9 are emitted from the sample 5. The configuration shown in FIG. 2 is the same as the configuration shown in FIG. 1. In FIG. 2, secondary electrons 10 are emitted from the sample 5. The operation of the apparatus constructed in this way is described below.

The primary electron beam 2 produced from the electron source 1 is shaped into a perfectly circular cross section by the beam-shaping aperture 7 having a hole 7a. After the current of the primary electron beam is limited, the beam is focused by the condenser lens 3. One crossover point C is formed between the objective lens 4 and the condenser lens 3. The aperture 6 having the opening 6a larger in diameter than the primary electron beam 2 is mounted at the crossover point C. The beam 2 is passed through the aperture 6 and then sharply focused by the objective lens 4 onto the observed sample 5.

As shown in FIG. 1, the backscattered electrons 9 produced from the sample 5 to be observed describe substantially the same orbit as the primary electron beam 2 in the reverse direction. That is, the beam is focused by the objective lens 4 and forms a crossover point near the aperture 6. Then, the beam diverges. Subsequently, the beam is again focused slightly by the condenser lens 3. The backscattered electrons 9 are detected by the charged-particle detector 8.

The orbit of the secondary electrons is shown in FIG. 2. The secondary electrons 10 produced from the sample 5 are focused to a large extent by the objective lens 4 and spread greatly at the position of the aperture 6. The secondary electrons 10 hitting the aperture 6 are absorbed by the aperture 6. A very small part of the secondary electrons 10 passed through the opening 6a in the aperture 6 arrives at the charged-particle detector 8 but is limited by the aperture 6. Therefore, the arriving electrons hardly contribute to the image quality.

Therefore, the image obtained by the charged-particle detector 8 is a backscattered electron image. As a result, only the backscattered electrons 9 can be separated out and detected. Where the charged-particle detector 8 is designed to be highly sensitive to low-energy electrons, secondary electrons hardly contribute to the image. Consequently, a backscattered electron image can be derived. In this way, a backscattered electron image of low-energy electrons can be obtained, which has been heretofore impossible to achieve.

Second Embodiment

Figure 3:
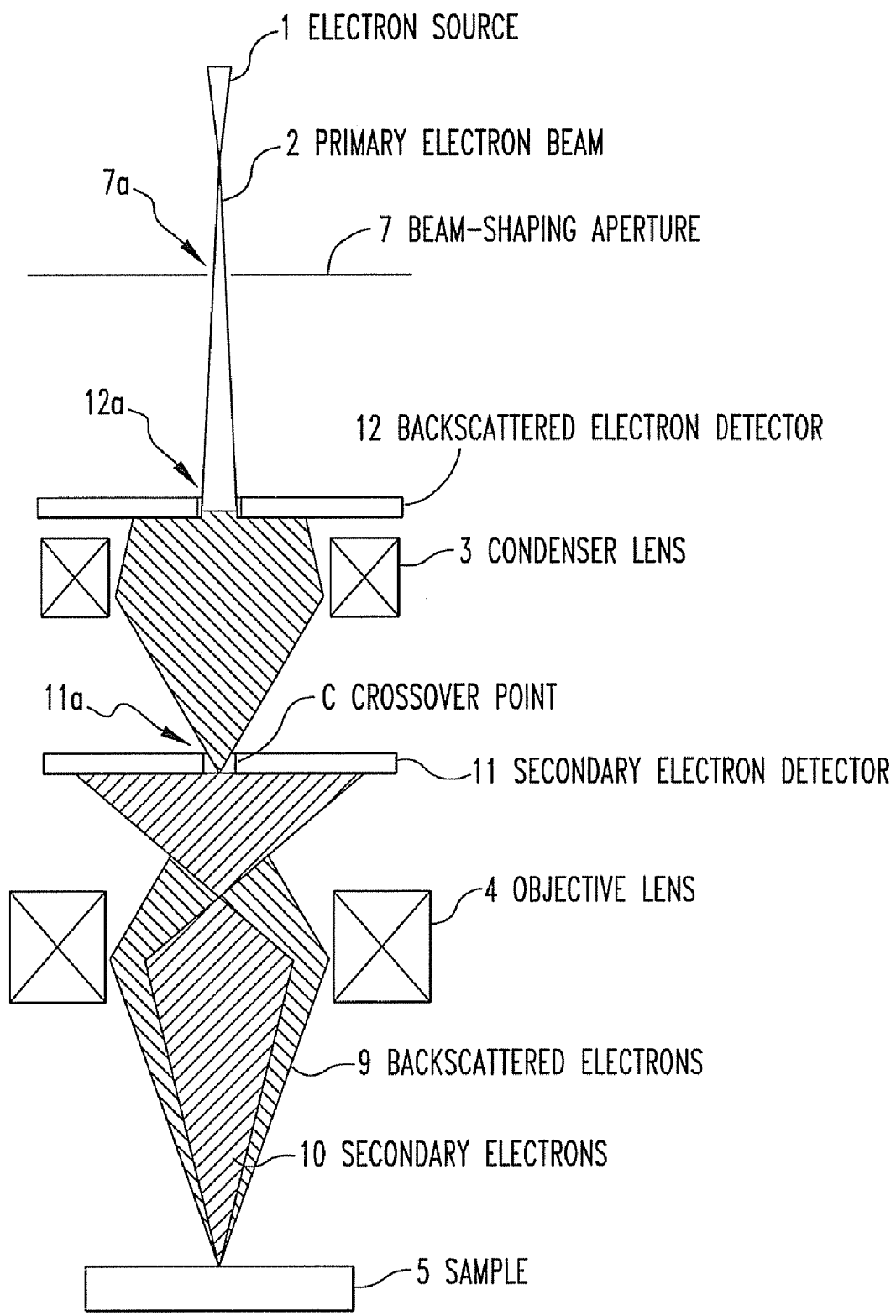
FIG. 3 is a diagram illustrating simultaneous detection of backscattered electrons and secondary electrons in the second embodiment of the present invention.

FIG. 3 illustrates simultaneous detection of backscattered electrons and secondary electrons in a second embodiment of the present invention. In FIGS. 1, 2, and 3, identical components are indicated by identical reference numerals. The scanning optics are omitted also in FIG. 3. In FIG. 3, an electron source 1 produces an electron beam 2. The beam 2 produced from the electron source 1 is focused onto an observed sample 5 by an objective lens 4. At least one condenser lens 3 is disposed between the electron source 1 and the objective lens 4. The beam 2 is shaped into a perfectly circular cross section by a beam-shaping aperture 7 that also acts to limit the current of the primary electron beam 2.

The condenser lens 3 operates such that the primary electron beam 2 forms one crossover point between the condenser lens 3 and the objective lens 4. A secondary electron detector 11 is mounted near the crossover point C of the primary electrons 2 and acts as a first charged-particle detector. A backscattered electron detector 12 is mounted at a position closer to the electron source than the crossover point and acts as a second charged-particle detector. The backscattered electron detector 12 is provided with a hole 12a. The secondary electron detector 11 is provided with a hole 11a. The aperture 6 (FIG. 2) having a function of absorbing secondary electrons is utilized as the secondary electron detector 11. Backscattered electrons 9 are emitted from the observed sample 5. Secondary electrons 10 are emitted from the sample 5. The operation of the apparatus constructed in this way is described below.

The primary electron beam 2 produced from the electron source 1 is shaped into a perfectly circular cross section by the beam-shaping aperture 7. Then, the beam is focused by the condenser lens 3 and forms one crossover point C between the condenser lens 3 and the objective lens 4. The secondary electron detector 11 having an aperture larger in diameter than the primary electron beam 2 is mounted at the crossover point C. The beam 2 passes through the secondary electron detector 11 and then is sharply focused onto the sample 5 by the objective lens 4.

As shown in FIG. 3, the backscattered electrons 9 emitted from the observed sample 5 describe substantially the same orbit as the primary electron beam 2 in the reverse direction. That is, the beam is focused by the objective lens 4, forms a crossover point near the secondary electron detector 11, and diverges. Then, the beam is again focused slightly by the condenser lens 3. The backscattered electrons 9 are detected at the position of the backscattered electron detector 12.

Meanwhile, the secondary electrons 10 are focused greatly by the objective lens 4 and spread greatly at the position of the secondary electron detector 11. The secondary electrons 10 hitting the secondary electron detector 11 create a scanned secondary electron image. A very small portion of the secondary electrons 10 passed through the opening in the secondary electron detector 11 arrives at the backscattered electron detector 12. However, the secondary electrons are limited by the opening (aperture) 11a in the secondary electron detector 11 and so hardly contribute to the image quality.

Therefore, the image obtained by the secondary electron detector 11 is a secondary electron image. The image obtained by the backscattered electron detector 12 is a backscattered electron image. If the backscattered electron detector 12 is designed to be sensitive to low-energy electrons, the secondary electrons 10 hardly contribute to the image. Consequently, a backscattered electron image can be derived. Hence, a low-energy backscattered electron image can be obtained which has been impossible to achieve in the past. At the same time, a secondary electron image can be obtained.

Third Embodiment

Figure 4:
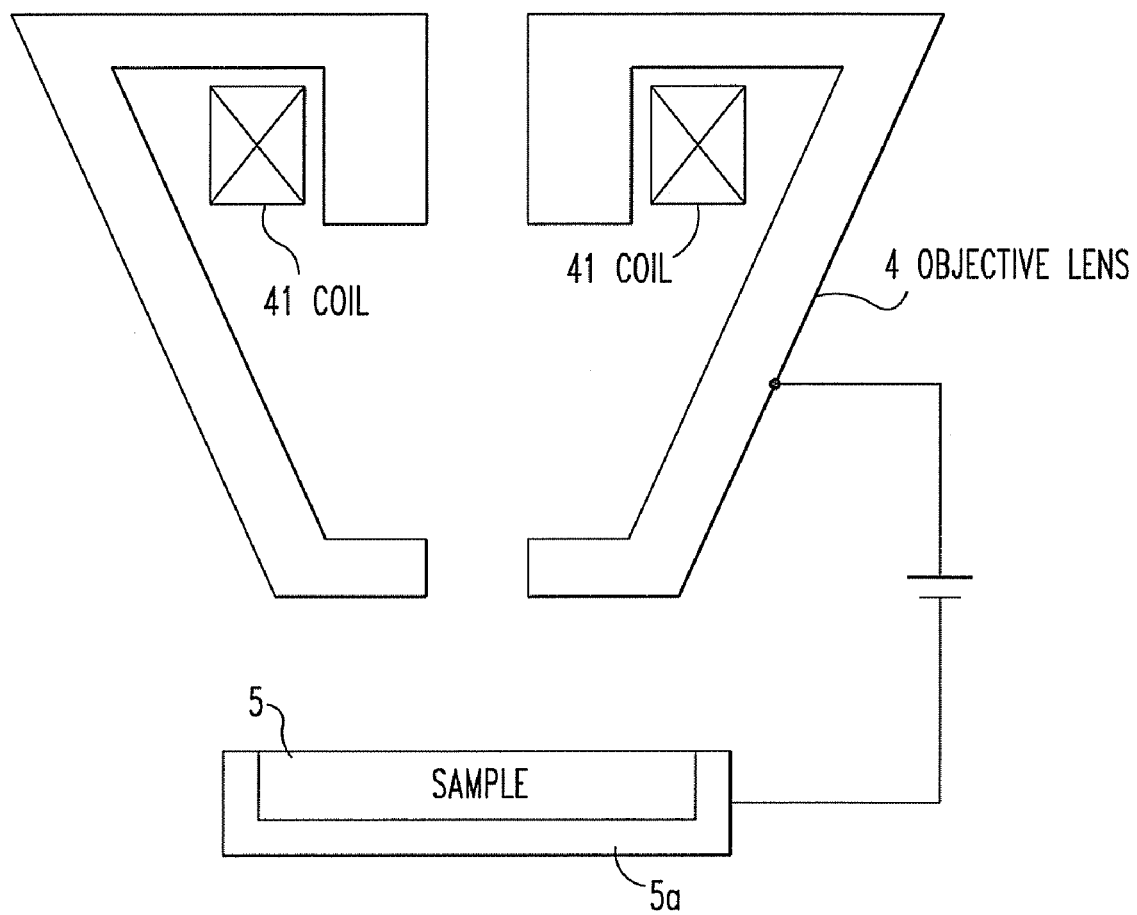
FIG. 4 is a diagram showing an example of structure of a cathode lens used in a third embodiment of the present invention.

In the above embodiments, a normal objective lens can be used as the objective lens 4. In order to obtain higher image quality, the structure of the objective lens 4 is contrived as follows. FIG. 4 shows an example of the structure of a cathode lens that is used as an objective lens in the present invention. In FIG. 4, the objective lens 4 is excited by a coil 41. A negative potential is applied to the observed sample 5 relative to the potential at the surface of the objective lens 4. As a result, the primary electron beam is converged by a decelerating field produced between the front end of the objective lens 4 and the sample 5. Consequently, a backscattered electron image or secondary electron image of the sample 5 with reduced aberration can be obtained.

Furthermore, according to the present invention, a combined magnetic objective lens-cathode lens can be used as the aforementioned objective lens. A potential difference is produced between the potential at the outer wall of the objective lens and a sample holder 5a. In this way, an image with still reduced aberration can be obtained.

In addition, according to the present invention, the objective lens can be made of a combined magnetic objective lens-decelerating electrostatic objective lens. A potential difference is produced between the outer wall of the objective lens and the inside of the objective lens. In this way, an image with reduced aberration can be obtained.

Additionally, according to the present invention, the objective lens is made of a combined magnetic objective lens-cathode lens. The magnetic objective lens is at ground potential. A high negative voltage is applied to the sample holder 5a. In this way, an image with reduced aberration can be obtained.

Moreover, according to the present invention, the primary electron beam can be shaped into a perfectly circular cross section by providing a beam-shaping aperture above the condenser lens. As a result, an accurate image can be obtained.

Figure 5:
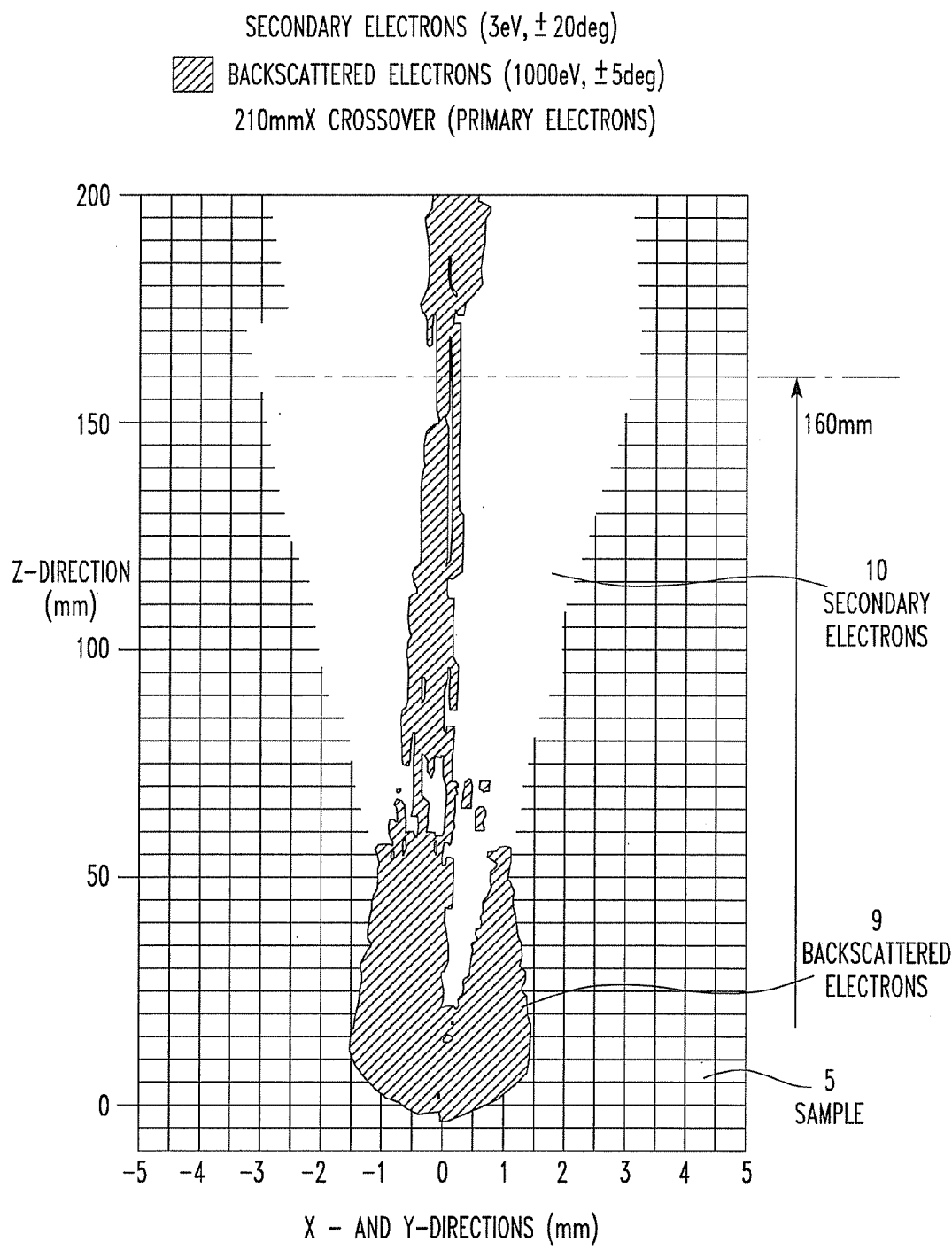
FIG. 5 is a diagram showing the results of simulations of orbits of secondary electrons and backscattered electrons.
Figure 6:
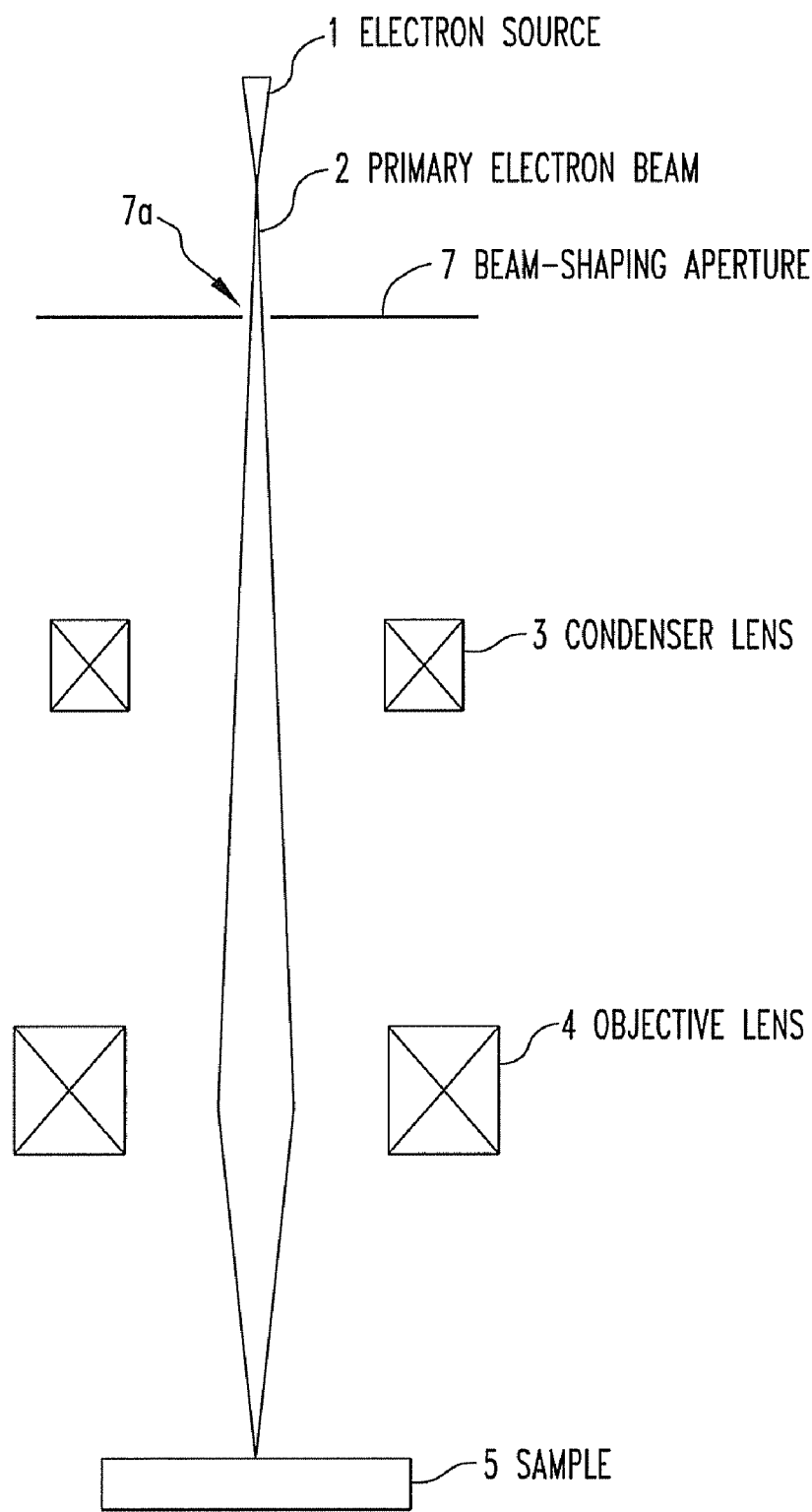
FIG. 6 is a diagram illustrating an example of configuration of a prior art electron optical system.
Figure 7:
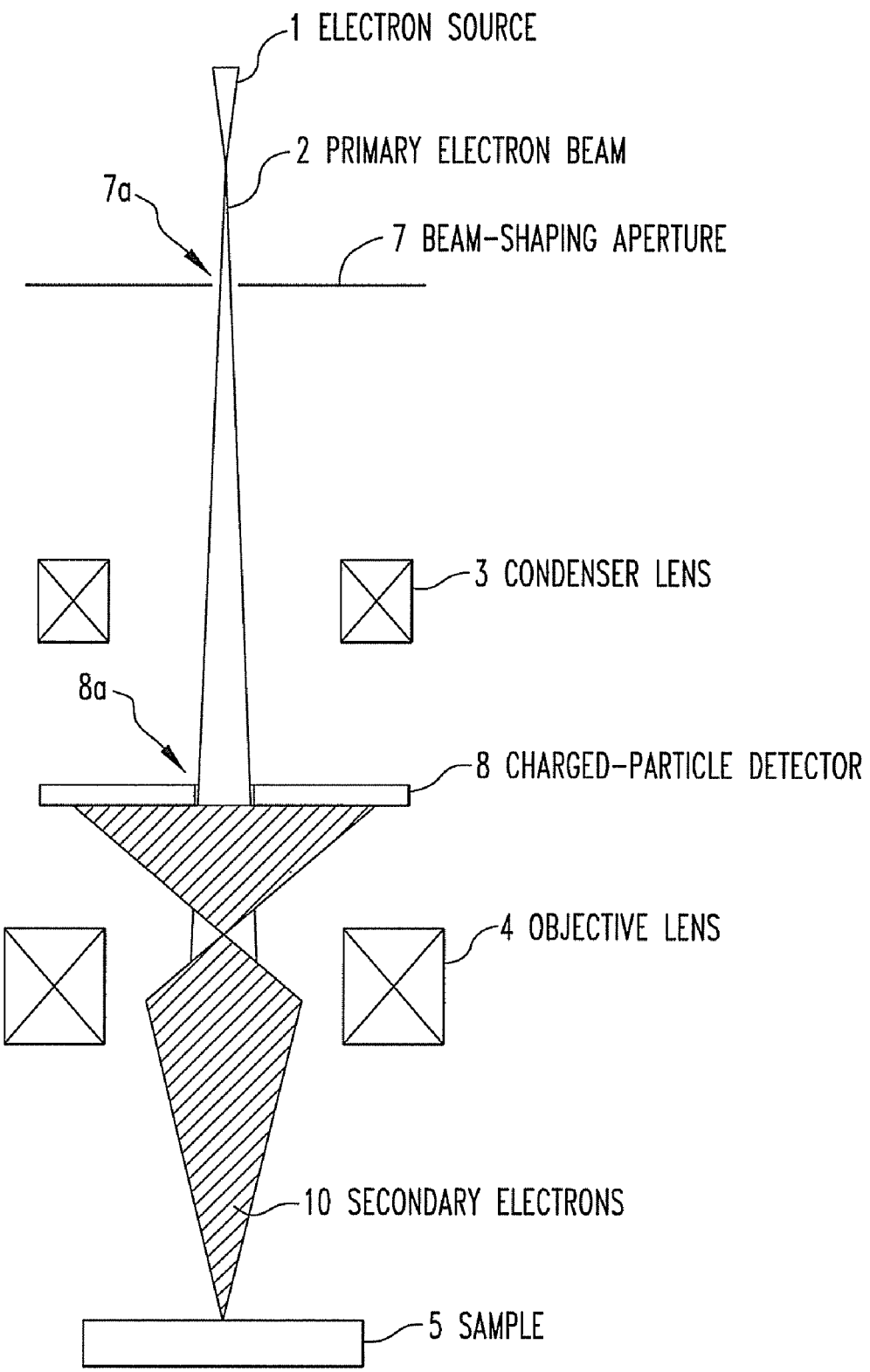
FIG. 7 is a diagram illustrating a prior art charged-particle detector and the orbit of secondary electrons.
Figure 8:
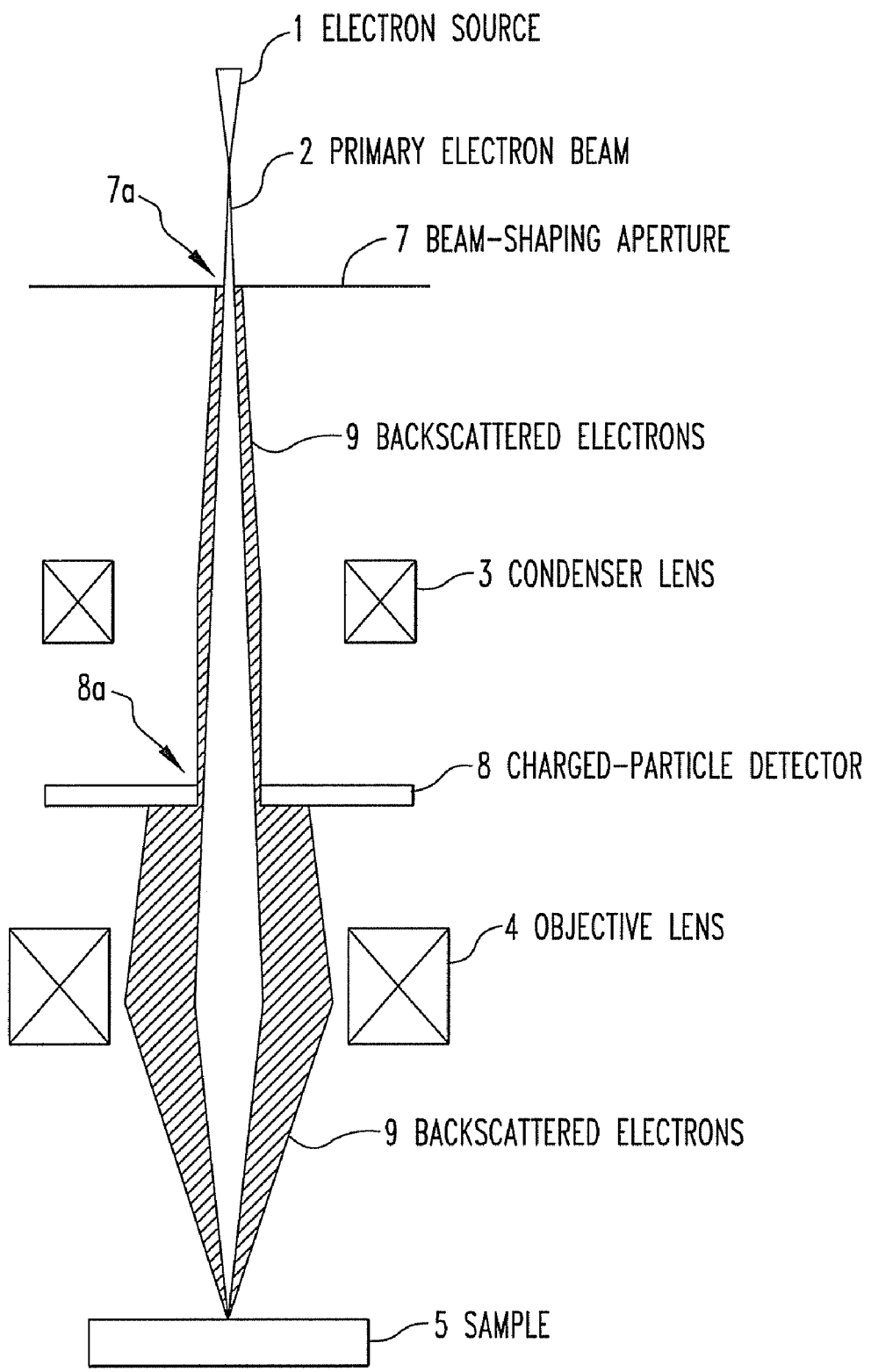
FIG. 8 is a diagram illustrating another prior art charged-particle detector and the orbit of backscattered electrons.

In FIG. 5, the results of simulations of secondary electron orbits and backscattered electron orbits are shown. In the graph of FIG. 5, the horizontal axis indicates the direction of the XY-plane. The vertical axis indicates the Z-direction. The numerical values in the graph are represented in mm. Backscattered electrons 9 have a crossover point at a distance of 160 mm above the sample 5. The primary electron beam 2 is made to create a crossover point at a distance of 210 mm above the sample 5. The difference of 50 mm is due to the spherical aberration in the objective lens 4 for the backscattered electrons 9. An aperture or secondary electron detector is disposed at a distance from 210 to 160 mm. A backscattered electron detector is mounted above the aperture or secondary electron detector.

In the past, there has been the problem that it is impossible to detect low-energy backscattered electrons. In contrast, a scanning electron microscope having an electron source producing a primary electron beam, an objective lens for focusing the beam onto an observed sample, at least one condenser lens disposed between the electron source and the objective lens, and a scanning deflector for scanning the beam in the x- and y-directions in two dimensions over the surface of the sample can detect low-energy backscattered electrons. The condenser lens is operated such that the primary electron beam forms one crossover point between the condenser lens and the objective lens. A charged-particle detector is mounted at a position closer to the electron source than the crossover point. An aperture having a diameter larger than that of the primary electron beam is mounted either at the crossover point or at a position closer to the sample than the crossover point.

Furthermore, in the past, there has been the problem that it is impossible to detect backscattered electrons and secondary electrons separately and simultaneously. In contrast, a scanning electron microscope having an electron source for producing an electron beam, an objective lens for focusing the beam onto an observed sample, at least one condenser lens disposed between the electron source and the objective lens, and a scanning deflector for scanning the primary electron beam in X- and Y-directions in two dimensions over the surface of the sample can detect backscattered electrons and secondary electrons separately and simultaneously. The condenser lens operates such that the primary electron beam forms one crossover point between the condenser lens and the objective lens. A first charged-particle detector is mounted at the crossover point or at a position closer to the sample than the crossover point. A second charged-particle detector is mounted at a position closer to the electron source than the crossover point.

Fourth Embodiment

Figure 9:
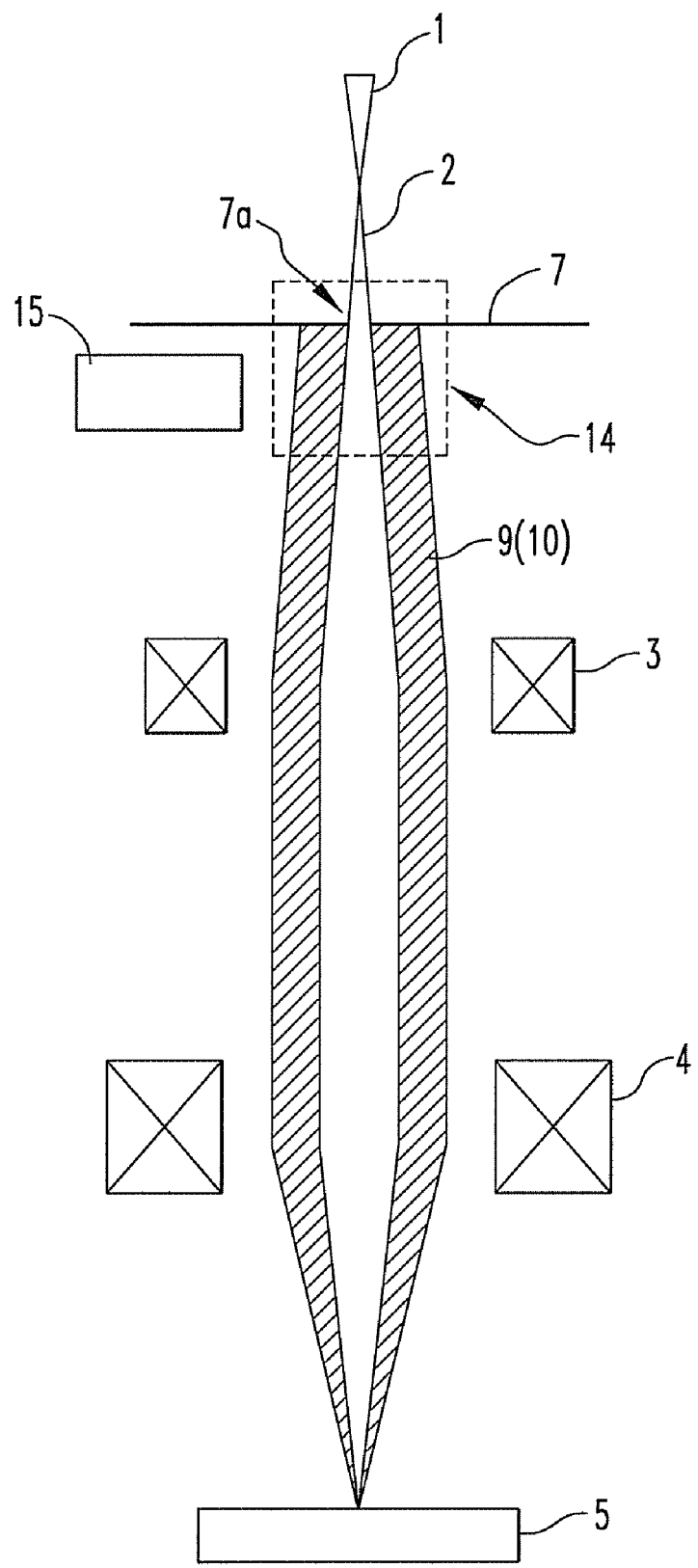
FIG. 9 is a schematic diagram of a beam apparatus according to a fourth embodiment of the present invention.

FIG. 9 is a schematic diagram showing a beam apparatus according to a fourth embodiment of the present invention. The beam apparatus has an electron source 1 producing a primary electron beam 2, an objective lens 4 for focusing the beam 2 onto an observed sample 5, a condenser lens 3 disposed between the electron source 1 and the objective lens 4, a beam-shaping aperture 7 disposed between the electron source 1 and the condenser lens 3, and a scanning deflector (not shown). The beam apparatus has the configuration of a scanning electron microscope.

The beam-shaping aperture 7 is provided with a hole 7a to permit passage of the primary electron beam 2. The diameter of the hole 7a is set to about 30 μm, which is sufficiently smaller than the diameter of the range of orbit of backscattered electrons produced from the sample 5.

An electron detector 15 is disposed on the side of the beam-shaping aperture 7 facing the sample 5 and near the beam-shaping aperture 7. Backscattered electrons 9 or secondary particles 10 produced secondarily from the sample 5 in response to the irradiation by the primary electron beam 2 arrive at the beam-shaping aperture 7, producing electrons from the beam-shaping aperture 7. These produced electrons are detected by the detector 15. The detected electrons are secondary electrons. A charged-particle detector (not shown) is disposed between the condenser lens 3 and the objective lens 4 and acts to detect secondary electrons produced from the sample 5 in response to the irradiation by the beam 2.

Figure 10:
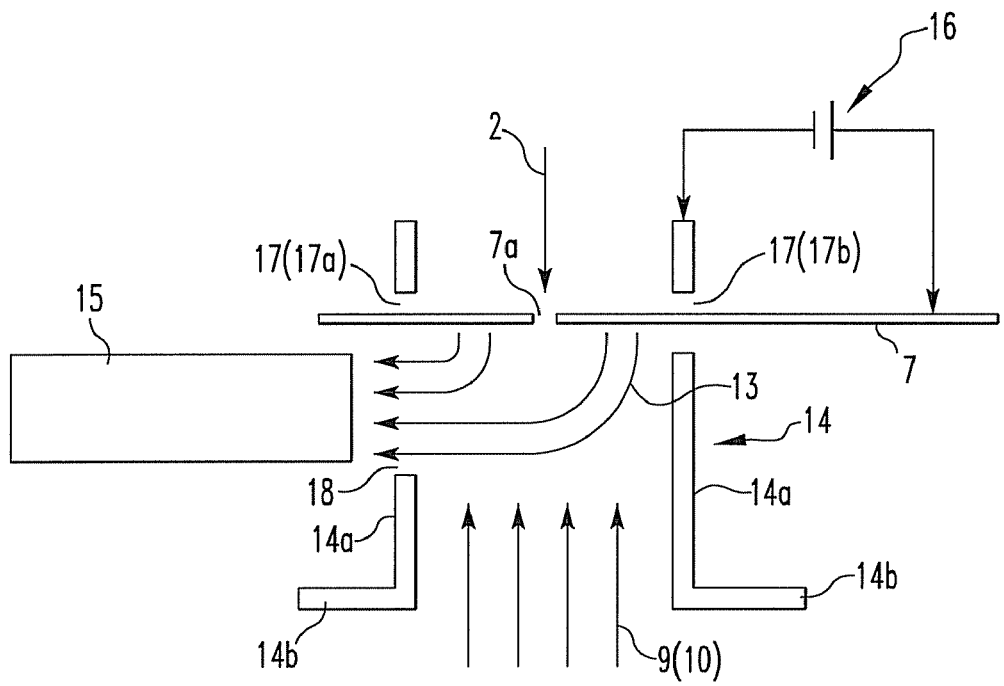
FIG. 10 is a cross-sectional view showing the structure of an electrode for use in the beam apparatus according to the fourth embodiment of the present invention.

An electrode 14 is arranged between the beam-shaping aperture 7 and the condenser lens 3. As shown in FIG. 10, the center axis of the electrode 14 is located on the optical axis of the primary electron beam 2 emanating from the electron source 1. The electrode 14 is a hollow, annular electrode having an opening 18 in the portion of the side surface 14a of the electrode 14 located opposite to the detector 15.

The beam-shaping aperture 7 can move in a direction perpendicular to the optical axis of the primary electron beam 2. Two slits 17a and 17b permitting passage of the beam-shaping aperture 7 during its movement are formed in the side surface 14a of the electrode 14. The slits 17a and 17b are located opposite to each other. The slit 17a has an intermediate portion located on the side of the detector 15, the intermediate portion being connected with the upper end of the opening 18 formed under the intermediate portion.

A flange 14b is formed at the lower end of the electrode 14 on the side of the sample 5. The flange 14b is connected with the flange (not shown) of a liner tube (not shown).

The electrode 14 is made of phosphor bronze or aluminum because phosphor bronze and aluminum are nonmagnetic materials and are electrically conductive. If the electrode 14 is made of a magnetic material, the primary electron beam 2 will be deflected unwantedly with undesirable results.

A power supply 16 applies a given negative potential to the electrode 14 with respect to the beam-shaping aperture 7. The potential is set within a range of from −10 V to 0 V. The beam-shaping aperture 7 is at ground potential.

Figure 11:
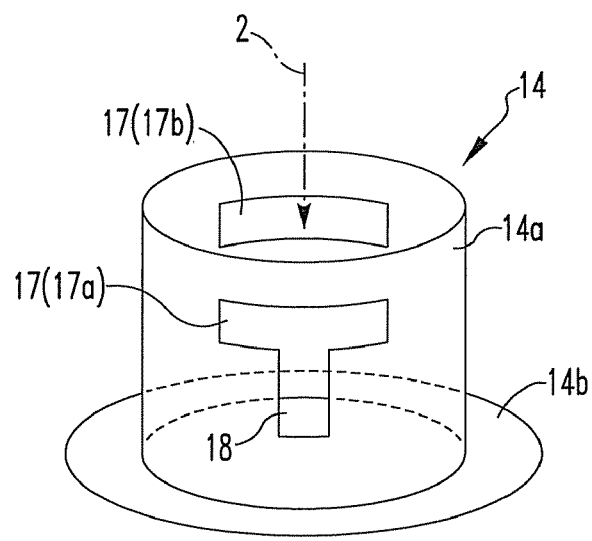
FIG. 11 is a perspective view showing the structure of the electrode for use in the beam apparatus according to the fourth embodiment of the present invention.

As a reference, a perspective view of the electrode 14 as viewed from the side of the electron detector 15 is shown in FIG. 11. In this figure, the thicknesses of various portions of the electrode 14 are not shown. The operation of the beam apparatus constructed in this way according to the present invention is described below.

The primary electron beam 2 emitted from the electron source 1 is accelerated to a given accelerating voltage and then shaped into a perfectly circular cross section by the electron beam-shaping aperture 7. The beam 2 is focused by the objective lens 4. The beam 2 is brought to a focus at the surface of the observed sample 5. Under this condition, the beam 2 is scanned over the surface of the sample 5 by a deflection scanner (not shown). As a result, the beam 2 is made to hit the surface of the sample 5.

Backscattered electrons 9 produced from the sample 5 in response to the irradiation by the electron beam 2 are passed through the objective lens 4, the charged-particle detector (not shown) for detecting secondary electrons emanating from the sample 5, and the condenser lens 3, and arrive at the beam-shaping aperture 7.

As described previously, the diameter of the hole 7a formed in the beam-shaping aperture 7 is sufficiently smaller than the diameter of the range of orbit of the backscattered electrons 9. Therefore, the backscattered electrons 9 arriving at the beam-shaping aperture 7 collide against the surroundings of the hole 7a in the aperture 7.

In this way, secondary electrons 13 that are particles to be detected are produced from the portions of the beam-shaping aperture 7 against which the backscattered electrons 9 collided as shown in FIG. 10.

The power supply 16 applies the aforementioned negative potential to the electrode 14 shown in FIG. 10 with respect to the beam-shaping aperture 7 that is at ground potential. An electric field is produced inside the electrode 14 to which the negative potential is applied in this way.

The portion of the side surface 14a of the electrode 14 opposite to the electron detector 15 is provided with the opening 18. The presence of the opening 18 makes asymmetric the electric field near the optical axis of the primary electron beam 2 inside the electrode 14. As a result, the electric field acts as a deflection electric field that attracts the secondary electrons 13 toward the detector 15 through the opening 18. Consequently, the secondary electrons 13 produced from the beam-shaping aperture 7 can be detected by the electron detector 15 efficiently.

Figure 12:
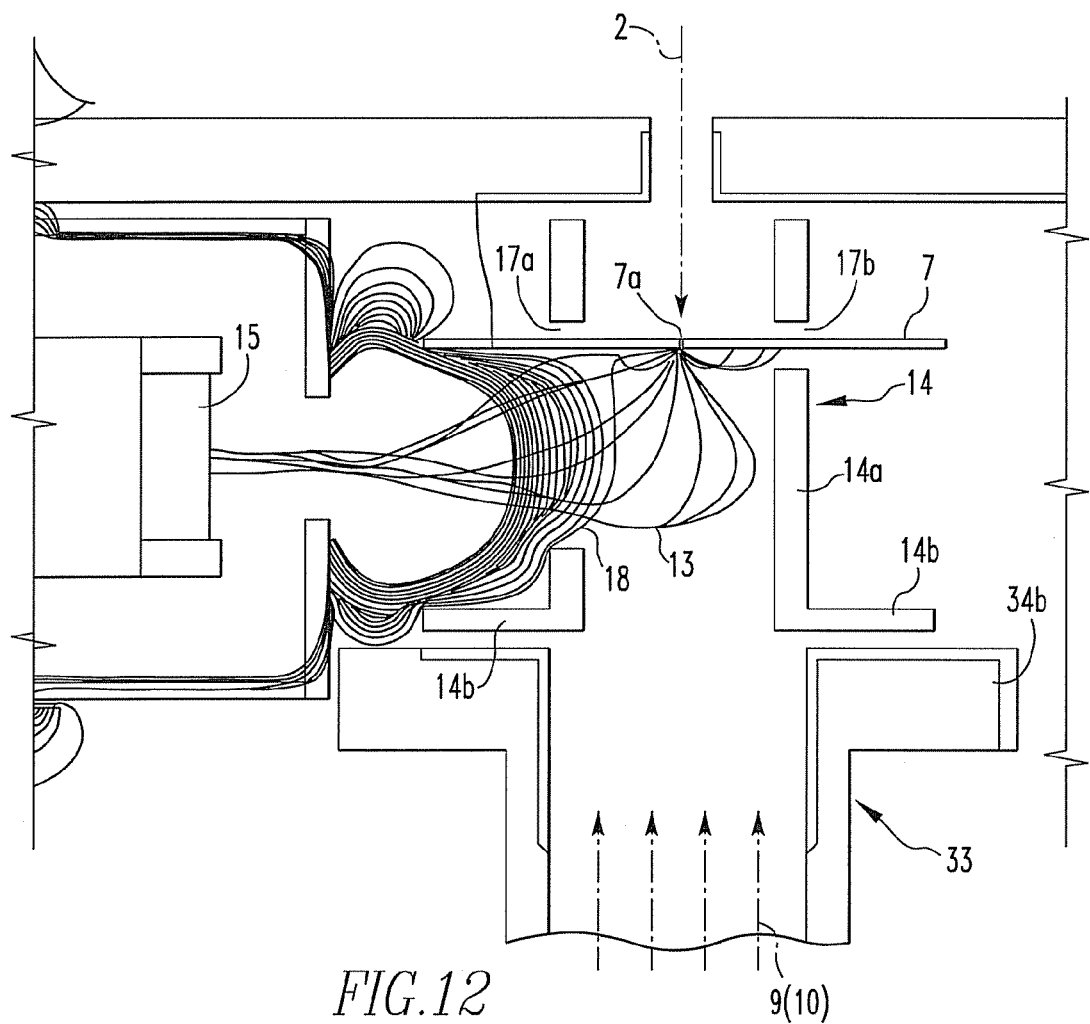
FIG. 12 is a diagram illustrating simulations in the fourth embodiment of the present invention.

FIG. 12 shows the results of simulations of a method in which a voltage was applied to the electrode 14 by the power supply 16 such that the electrode 14 was put at a negative potential with respect to the beam-shaping aperture 7 at ground potential.

The efficiency at which the secondary electrons 13 were detected by the electron detector 15 was about 6% when the voltage applied to the electrode 14 was 0 V, i.e., at the same potential as the beam-shaping aperture 7.

On the other hand, when the voltage applied to the electrode 14 was set to −3 V, the detection efficiency was improved to nearly 80%.

Accordingly, it is advantageous to apply a negative potential to the electrode 14 with respect to the potential at the beam-shaping aperture 7. Preferably, the applied potential is set within a range of from −10 V to 0 V.

The magnitude of the deflection electric field formed inside the electrode 14 when a negative potential falling in this range is applied to the electrode 14 is so small that the orbit of the primary electron beam 2 having energies of hundreds of eV to several keV is little affected. Therefore, the efficiency at which the secondary electrons 13 are detected by the detector 15 can be improved without increasing the deflection aberration in the primary electron beam 2. If the potential is set lower than −10 V, the electric field produced by the front end of the electron detector 15 to attract the secondary electrons 13 to the detector 15 will be affected, thus deteriorating the efficiency at which the secondary electrons 13 are detected. Consequently, the potential is preferably set within a range of from −10 V to 0 V.

Referring to FIG. 12, there is shown a liner tube 33 connected with a condenser lens and an objective lens (none of which are shown) located in the later stage. The flange 14b of the electrode 14 is bolted or otherwise fastened to the flange 24 of the liner tube 33.

Figure 13:
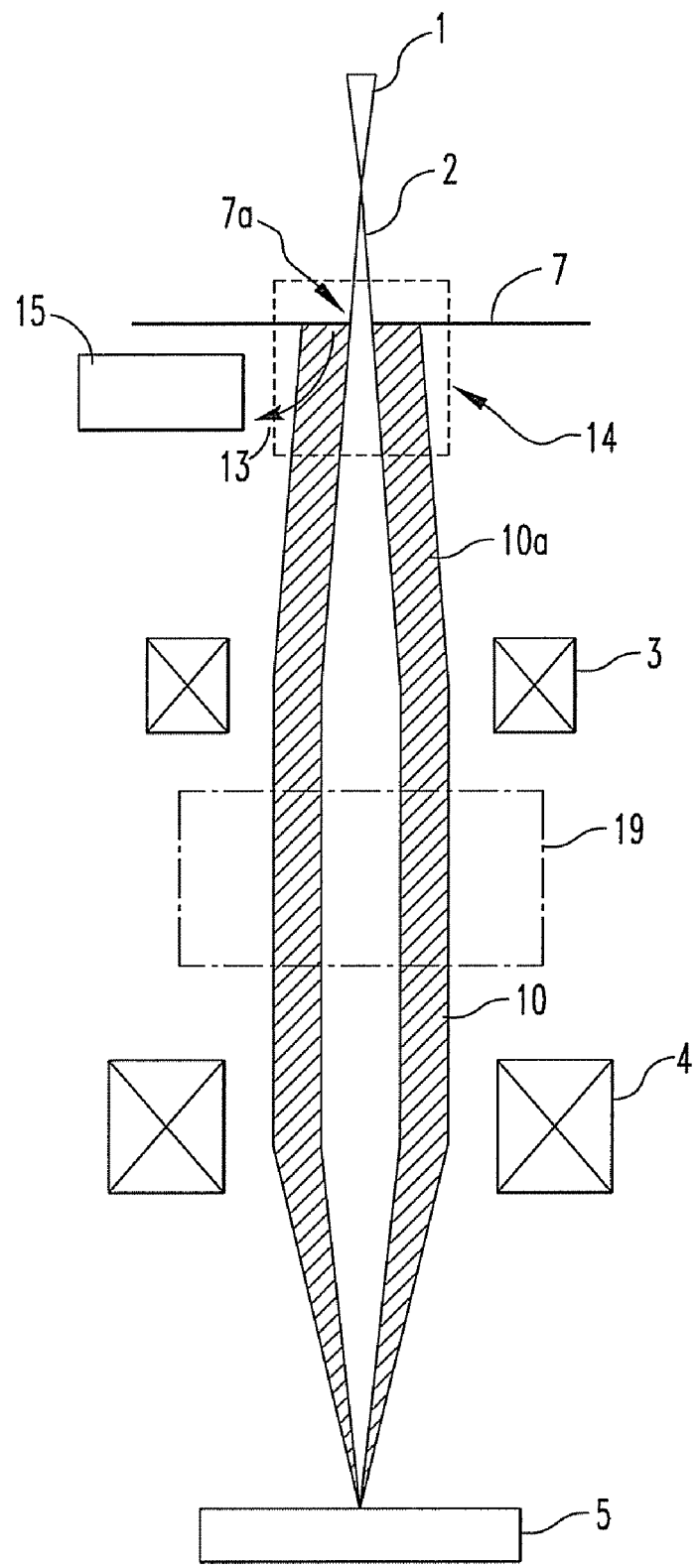
FIG. 13 is a schematic diagram showing a first modification of the fourth embodiment of the present invention.

A first modification of the fourth embodiment is next described by referring to FIG. 13. The present modification is similar in fundamental structure with the above-described fourth embodiment except that an energy filter 19 is arranged between the condenser lens 3 and the objective lens 4.

The present modification is similar in operation with the above-described fourth embodiment. The secondary particles 10 produced from the observed sample 5 and arriving at the beam-shaping aperture 7 contain, in practice, backscattered electrons including elastically-backscattered electrons and multiple scattering electrons having energies smaller than those of the elastically-backscattered electrons. In some cases, the secondary particles may contain secondary electron components. The elastically-backscattered electrons are those of backscattered electrons which have energies almost equal to those of the electrons of the primary beam.

In this case, in order to form a scanned image based on elastically-backscattered electrons by extracting only the elastically-backscattered electrons, for example, from the secondary particles 10 consisting mainly of backscattered electrons and detecting the extracted elastically-backscattered electrons, the secondary particles 10 produced from the observed sample 5 are passed through the energy filter 19. Thus, only the elastically-backscattered electrons 10a are extracted.

The extracted, elastically-backscattered electrons 10a are made to reach the beam-shaping aperture 7. Secondary electrons 13 are produced from the aperture 7 at which the elastically-backscattered electrons 10a arrive. The secondary electrons 13 are detected by the electron detector 15.

In this way, a scanned image based on the elastically-backscattered electrons 10a can be obtained. The backscattered electrons 10a are secondary signals in which information about the compositional contrast (compositional difference) of the observed sample 5 is reflected much. In the scanned image obtained based on the elastically-backscattered electrons 10a, the compositional contrast is shown clearly.

The energies of the elastically-backscattered electrons 10a are substantially equal to the energies of the primary electron beam 2 and so the intensity of the energy filter 19 is so set that the secondary particles 10 having energies lower than the energies of the electrons of the primary electron beam 2 can be deflected so as not to arrive at the beam-shaping aperture 7.

For example, a Wien filter configuration can be used as the configuration of the energy filter 19. Instead of this configuration, an electric deflector or magnetic deflector can be used.

Figure 14:
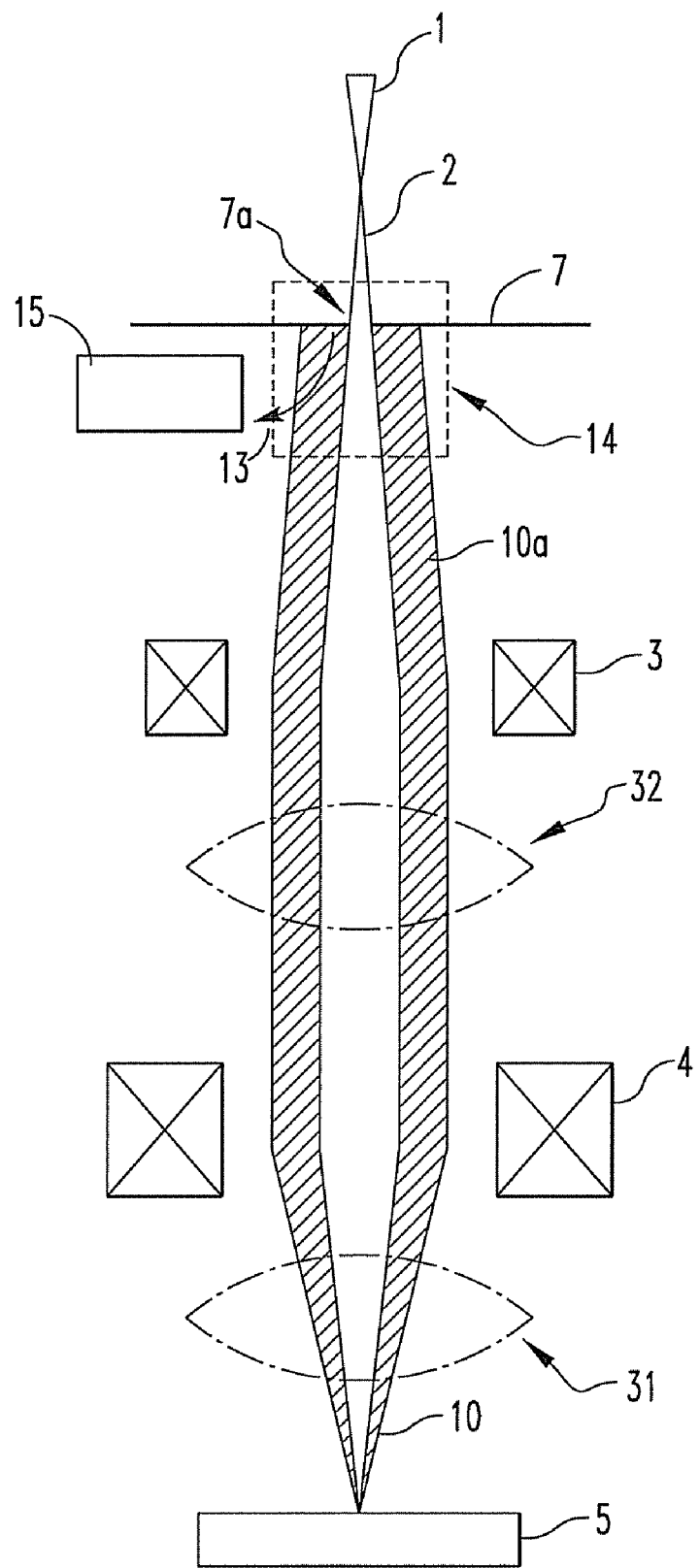
FIG. 14 is a schematic diagram showing a second modification of the fourth embodiment of the present invention.

A second modification of the fourth embodiment is next described by referring to FIG. 14. In the present modification, a lens pair consisting of a decelerating lens 31 and an accelerating lens 32 is provided instead of the energy filter used in the first modification.

In FIG. 14, the decelerating lens 31 is mounted between the objective lens 4 and the observed sample 5. The accelerating lens 32 is mounted between the condenser lens 3 and the objective lens 4.

In this configuration, the function of the accelerating lens 32 for focusing secondary electrons serves similarly to the energy filter.

Therefore, in this configuration, too, it is possible that only the elastically-backscattered electrons 10a are extracted from the secondary particles 10 and reach the beam-shaping aperture 7. The secondary electrons 13 are produced from the aperture 7 at which the elastically-backscattered electrons 10a arrive. The secondary electrons 13 are detected by the electron detector 15. A scanned image based on the elastically-backscattered electrons 10a can be acquired.

The beam apparatus according to the present embodiment has the beam source 1 for emitting the primary electron beam 2, the objective lens 4 for focusing the primary electron beam 2 released from the beam source 1 onto the sample 5, and the aperture 7 disposed between the beam source 1 and the objective lens 4. The beam apparatus further includes the detector 15 for detecting the particles 13 produced from the aperture 7 by an interaction between the secondary particles 10 and the aperture 7 after the secondary particles 10 produced secondarily from the sample 5 in response to the irradiation by the beam 2 arrive at the aperture 7. The apparatus further includes the hollow detector (electrode) 14 whose center axis is located on the optical axis of the primary beam 2 emitted from the beam source 1. The opening 18 is formed in the side surface 14a of the electrode 14 opposite to the detector 15. The electric field produced by the electrode 14 acts to move the detected particles 13 from the aperture 7 toward the detector 15 through the opening 18. Thus, the moved particles 13 are detected by the detector 15.

The aperture 7 can move in a direction perpendicular to the optical axis. The electrode 14 is provided with the slits 17 (17a and 17b) through which the aperture 7 is passed. The flange 14b is formed at the end of the electrode 14 located closer to the sample 5.

A potential set within a range of from −10 V to 0 V with respect to the potential at the aperture 7 is applied to the electrode 14. The electrode 14 is made of phosphor bronze or aluminum.

The secondary particles 10 are backscattered electrons. The detected particles 13 are secondary electrons.

The energy filter 19 may be mounted between the aperture 7 and the sample 5 such that certain secondary particles extracted by the energy filter 19 arrive at the aperture 7.

The decelerating lens 31 may be mounted between the objective lens 4 and the sample 5. The accelerating lens 32 may be mounted between the condenser lens 3 and the objective lens 4. Certain secondary particles extracted by the lens pair consisting of these decelerating lens 31 and accelerating lens 32 may be made to arrive at the aperture 7.

The extracted certain secondary particles may be elastically-backscattered electrons.

In this way, in the present embodiment, there is provided the detector 15 that detects particles 13 produced from the aperture 7 after the secondary particles 10 produced secondarily from the sample 5 in response to the irradiation by the primary beam 2 arrive at the aperture 7. The hollow electrode 14 whose center axis is located on the optical axis of the primary beam 2 emanating from the beam source 1 is mounted. The opening 18 is formed in the side surface 14a of the electrode 14 opposite to the detector 15. The electric field produced by the electrode 14 acts to move the particles 13 from the aperture 7 toward the detector 15 through the opening 18. In consequence, the moved particles 13 are detected by the detector 15.

The electric field produced by the electrode 14 can attract the particles 13 to be detected toward the detector 15. Accordingly, a signal produced based on the secondary particles 10 (particles 13 to be detected) arriving at the aperture 7 from the sample 5 can be detected efficiently. As a result, the secondary particles 10 can be detected efficiently.

Therefore, where the secondary particles 10 are backscattered electrons, the signal produced based on the backscattered electrons can be detected efficiently. As a result, the backscattered electrons can be detected efficiently.

Having thus described our invention with the detail and particularity required by the Patent Laws, what is desired protected by Letters Patent is set forth in the following claims.

The invention claimed is:

1. A beam apparatus in which backscattered electrons are detected comprising:
a beam source for producing a primary beam;
an objective lens for focusing the primary beam produced from the beam source onto a sample;
at least one condenser lens disposed between the beam source and the objective lens and operating such that the primary beam forms one crossover point between the condenser lens and the objective lens;
an aperture plate positioned on the optical axis of the primary beam to block the orbit of secondary electrons emitted from the sample, the aperture plate having an opening through which the primary beam passes and being mounted at the crossover point or a position between the crossover point and the objective lens; and
a charged-particle detector positioned to detect backscattered electrons emitted from the sample and passed through the opening of the aperture plate, the charged-particle detector being mounted at a position closer to the beam source than the crossover point.

2. A beam apparatus in which backscattered electrons are detected comprising:
a beam source for producing a primary beam;
an objective lens for focusing the primary beam produced from the beam source onto a sample;
at least one condenser lens disposed between the beam source and the objective lens and operating such that the primary beam forms one crossover point between the condenser lens and the objective lens;
a first charged-particle detector positioned on the optical axis of the primary beam to block the orbit of secondary electrons emitted from the sample for detecting the secondary electrons, the first charged-particle detector having an opening through which the primary beam passes and being mounted at the crossover point or at a position between the crossover point and the objective lens; and
a second charged-particle detector positioned on the optical axis of the primary beam to detect backscattered electrons emitted from the sample and passed through the opening of the first charged-particle detector, the second charged-particle detector being mounted at a position closer to the beam source than the crossover point.

3. A beam apparatus in which backscattered electrons are detected comprising:
a beam source for producing a primary beam;
an objective lens for focusing the primary beam produced from the beam source onto a sample;
at least one condenser lens disposed between the beam source and the objective lens and operating such that the primary beam forms one crossover point between the condenser lens and the objective lens; and
a charged-particle detector positioned on the optical axis of the primary beam to detect secondary electrons emitted from the sample, the charged-particle detector having an opening through which backscattered electrons from the sample pass as well as the primary beam passes and being mounted at the crossover point or at a position between the crossover point and the objective lens.

4. A beam apparatus as set forth in any one of claims 1 to 3, wherein said objective lens is a magnetic objective lens.

5. A beam apparatus as set forth in any one of claims 1 to 3, wherein said objective lens is a cathode lens, and wherein a potential difference is produced between an outer wall of an electron optical column and a sample holder.

6. A beam apparatus as set forth in any one of claims 1 to 3, wherein said objective lens is a combined magnetic objective lens-cathode lens, and wherein a potential difference is produced between an outer wall of the objective lens and a sample holder.

7. A beam apparatus as set forth in any one of claims 1 to 3, wherein said objective lens is a combined magnetic objective lens-decelerating electrostatic objective lens, and wherein a potential is produced between an outer wall of the objective lens and the inside of the objective lens.

8. A beam apparatus as set forth in any one of claims 1 to 3, wherein said objective lens is a combined magnetic objective lens-cathode lens, and wherein the objective lens is at ground potential and a high voltage is applied to a sample holder.

9. A beam apparatus as set forth in any one of claims 1 to 3, wherein a beam-shaping aperture is mounted between said beam source and said condenser lens.

\* \* \* \* \*